United States Patent [19]

Hureau

[11] Patent Number: Plant 7,563

[45] Date of Patent: Jun. 18, 1991

[54] STRAWBERRY PLANT NAMED DARLIBELLE

[75] Inventor: Robert C. Hureau, Le Vaudoue, France

[73] Assignee: Societe Civile Darbonne, Milly-La-Foret, France

[21] Appl. No.: 407,049

[22] Filed: Sep. 14, 1989

[51] Int. Cl.[5] ..... A01H 5/00

[52] U.S. Cl. ..... Plt./49

[58] Field of Search ..... Plt./48, 49

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct strawberry plant named Darlibelle particularly characterized by its vigorous growth habit, erect leaves, early to medium season variety, medium size red fruit having a firm surface and a very firm and juicy flesh, and its disease resistance.

3 Drawing Sheets

1

The present invention relates to a new and distinctive variety of strawberry plant referred to by the varietal name Darlibelle.

The new cultivar is a product of a planned breeding program. The basic objective of the breeding program was to create a new variety of strawberry having good color, attractive shape, good productivity and good keeping quality.

The new variety was originated from a cross made by the inventor in a controlled breeding program in Milly-La-Foret, France. The female parent was a variety designated Gariguette, and the male parent was a variety designated Aiko.

Darlibelle was discovered and selected by the inventor as a plant within the progeny of the stated cross in a controlled environment in Milly-La-Foret, France. Asexual reproduction of the new variety, as performed by the inventor at Milly-La-Foret, France, has demonstrated that the combination of characteristics as herein disclosed for the new variety are firmly fixed and are retained through successive generations of asexual reproduction. The method of asexual reproduction used as the tissue culturing of the first selected plant, followed by propagation via runner production in a nursery.

Darlibelle has not been observed under all possible environmental conditions. The phenotype may vary significantly with variations in environment. The following observations, measurements and values describe plants grown in Milly La Foret, France, under conditions which closely approximate those generally used in commercial practice.

The following traits have been repeatedly observed and are determined to be basic characteristics of Darlibelle, which, in combination, distinguish this strawberry plant as a new and distinct variety:

1. Very vigorous habit
2. Erect leaves
3. Early to medium season variety
4. Medium size fruit
5. Bright red fruit
7. Fruit very resistant to Oidium disease These traits of Darlibelle may be distinguished from Darline and Gariguette, as follows:

2

| CHARACTERISTICS | DARLIBELLE | DARLINE | GARIGUETTE |
|---|---|---|---|
| Plant vigor | Very vigorous | Vigorous | Vigorous |
| Leaf habit | Erect | Erect | Less erect |
| Fruit size | Medium long and medium large | long and large | Very long and medium large |
| Fruit color | Bright red to purple | Orange red | Orange red to orange |
| Fruiting period | Early to mid season | Mid season | Very early |
| Picking duration | 5–6 weeks | 6–7 weeks | 4–5 weeks |
| Adaptation to soil | Adapted to all kinds of soils | Adapted to all kinds of soils | Needs soils with high clay level |
| Tolerance to diseases | Tolerant to Oidium and Botrytis | Tolerant to None Phytophthora Cactorum | |

The new variety is most similar to the female parent Gariguette, being similar thereto in the characteristics of upright corolla and resistant epidermis. Darlibelle is primarily distinguished from Gariguette as follows. Darlibelle is more vigorous, has a taller plant habit, and produces fruit later than Gariguette, and for a longer period. The fruit of Darlibelle is shorter and less acidic than that of Gariguette.

The accompanying color photographic drawings show typical leaves and fruit of specimen plants of the new variety.

Sheet 1 is a perspective view of a bed of plants of Darlibelle, showing both ripened and unrippened fruit.

Sheet 2 is a color photograph showing several whole berries, and sections of berries to show flesh formation and color.

Sheet 3 is a color photograph showing in plan view and in actual size typical leaves of Darlibelle.

The colors appearing in the photographs are as true as possible with color illustrations of this type. Color references are to The Royal Horticultural Society Color chart, (R.H.S.) or to the pantone matching system (PMS) 747XR, or where terms of ordinary dictionary significance are used.

Parentage:

*Male parent.*—Aiko.

*Female parent.*—Gariguette.

Propagation: Daribelle, when planted in a nursery in March, produces from 60–70 runners by November. The sizes of the runners range at the ground surface from 9 to 11 millimeters. Darlibelle runners develop a good rooting system, and provide vigorous vegetation in the nursery. Darlibelle produces more runner plants than Gariguette.

PLANTS:

A. Overall size: Large and globose, Darlibelle is a more vigorous plant than either Gariguette or Darline.

B. General plant habit:

1. *Preferred planting.*—In Milly-La-Foret, France is early July for summer planting, with peak production in early June.
2. *Plant habit.*—Globose.
3. *Plant density.*—Dense.
4. *Plant vigor.*—Strong.

C. Leaves:

1. *Size.*—Mature leaves medium to large, larger than Gariguette or Darline, approximately 8–13 cm long and 7–11 cm wide.
2. *Shape.*—Slightly oblong, more planar than Giriguette,a nd with less acute teeth, with the edges having wide serrations.
3. *Color.*—Upper surface, dark green, approximately 137A adult leaves are of a darker green at the bottom and a lighter green at the top, Darlibelle is a darker green than either Gariguette or Darline.
4. *Growth habit.*—3 leaflets the same as for Gariguette and Darline; more upright than Gariguette, but similar to Darline.
5. *Leaf cross section.*—Concave.
6. *Leaf blistering.*—Medium more blistering habit than Gariguette.
7. *Terminal leaflet length/width ratio.*—Slightly longer than broad. a. Shape of base: acute. b. Shape of tip: obtuse.
8. *Petiole.*—Position of hairs, upwards, slightly longer than Gariguette or Darline, 320–400 mm, with a diameter of 3.5 to 4 mm.
9. *Stipule anthocyanin coloration.*—Less than Less than that of Gariguette, but more than that of Darline; anthocyanin pigmentation on the edges is 184 C (PMS), composed of warm red, rubine red and trans. white; pigmentation in the center, depending on the state of ripeness, is a blend of 584 U (PMS), composed of yellow, reflex blue and trans. white, and 585 U (PMS), composed of yellow, reflex blue and trans. white.
10. *Stolons.*—Numerous. a. Anthocyanin coloration — weak to medium. b. Thickness — medium. c. Pubescence — weak.

INFLORESCENCE

A. Size and shape: Medium, free petals a little smaller than Gariguette or Darline, and having an obtuse shape.

B. Peduncles: Medium size, larger and longer than that of Gariguette, smaller and shorter than those of Darline.

C. Pedicel origination and form, and characteristics of hair: Medium; long pedicel with 3 to 4 indented upwardly directed hairs.

D. Abundance: Flowers nor proliferous, less abundant than for Gariguette, more abundant than for Darline; Darline will produce from 50–60 flowers per plant.

E. Color: Typical.

F. Anthers and pollen production: Very good production, less affected by low temperature than either Darline or Gariguette.

G. Calyx size, and sepal form and color: Calyx larger than corolla; sepall acute and green in color.

H. Position relative to foliage: Level.

I. Flower size: Medium.

J. Size of calyx relative to corolla: Smaller.

K. Size of inner calyx relative to outer: Larger.

L. Spacing of petals (on flowers with 5 or more petals): Free.

M. Petal length/width ratio: Petal length as long or slightly longer than width.

FRUIT

A. Overall size and shape (primary and secondary fruit):

*Primary fruits.*—Larger fruit (larger than those of Gariguette but smaller than those of Darline); conical to bi-conical, 19–28 grams, fruits are shorter than those of Gariguette.

*Secondary fruits.*—Identical shape as primary fruits, but smaller, 12–20 grams; larger and shorter than secondary fruits of Gariguette.

B. Seed characteristics: Level with surface.

C. Juiciness: Juicy.

D. Taste: Primary fruits have a weakened acidic taste; secondary fruits are sweeter in taste with more aroma, but less aroma than Gariguette.

E. Color, exterior and flesh: Bright red to purple with a strong glossiness, less orange than Gariguette; flesh is colored a light red with whitish veins, which are more visible than those of Gariguette.

F. Exterior surface:

1. *Glossy.*—Strong as strong as Gariguette but stronger than Darline.
2. *Shape.*—Conical shorter than Gariguette.
3. *Firm.*—Very firm firmer than Gariguette or Darline.

G. Characteristics of flesh and core: Very firm and juicy; medium to large core juicier and firmer than Gariguette, juicier than Darline; whitish core is more visible than that of Gariguette or Darline.

H. Keeping qualities: Remains glossy and firm keeps very well for 5–6 days after cooling at a temperature of 10° C., without rotting; resistent to bruises; darkens during storage, but keeps glossy; keeps better than Gariguette and slightly better than Darline.

I. Size: Medium.

J. Predominant shape: Conical, slightly larger than broad.

K. Time of ripening (50% of plants): Early.

L. Type of bearing: Partially remontant.

M. Fruiting truss attitude at first picking: Prostrate.

O. Difference in shape between primary and secondary fruit: Slight.

P. Band without achenes (seeds): Narrow.

Q. Surface: Slightly uneven.

R. Color: Red.

S. Evenness of color: Slightly uneven.

T. Glossiness: Strong.

U. Insertion of achenes (seeds): Level with surface.

V. Insertion of calyx: Set above fruit.

W. Position of calyx segments: Clasping or attached.

X. Calyx: Same size as fruit diameter.

Y. Adherence of calyx: Strong.

Z. Firmness: Very firm.

AA. Color of flesh: Generally lighter red, slightly uneven in color.

AB. Aroma: Primary fruits are weak in aroma, weaker than Gariguette, but similar to Darline; secondary fruits are sharper in aroma than the primary fruits, possessing less aroma than either Gariguette or Darline.

Disease resistance: Tolerant to Oidium and Botrytis.

General observations: Darlibelle is less affected by soil deficiencies than most of the commercial varieties, but will reduce its fruit production from an overdose of nitrogenous nutrients; the Darlibelle fruit remains attractive in the market, as does Darline, which makes it distinguishable from most existing commercial varieties.

I claim:

1. A new variety of strawberry plant named Darlibelle, as illustrated and described.

* * * * *

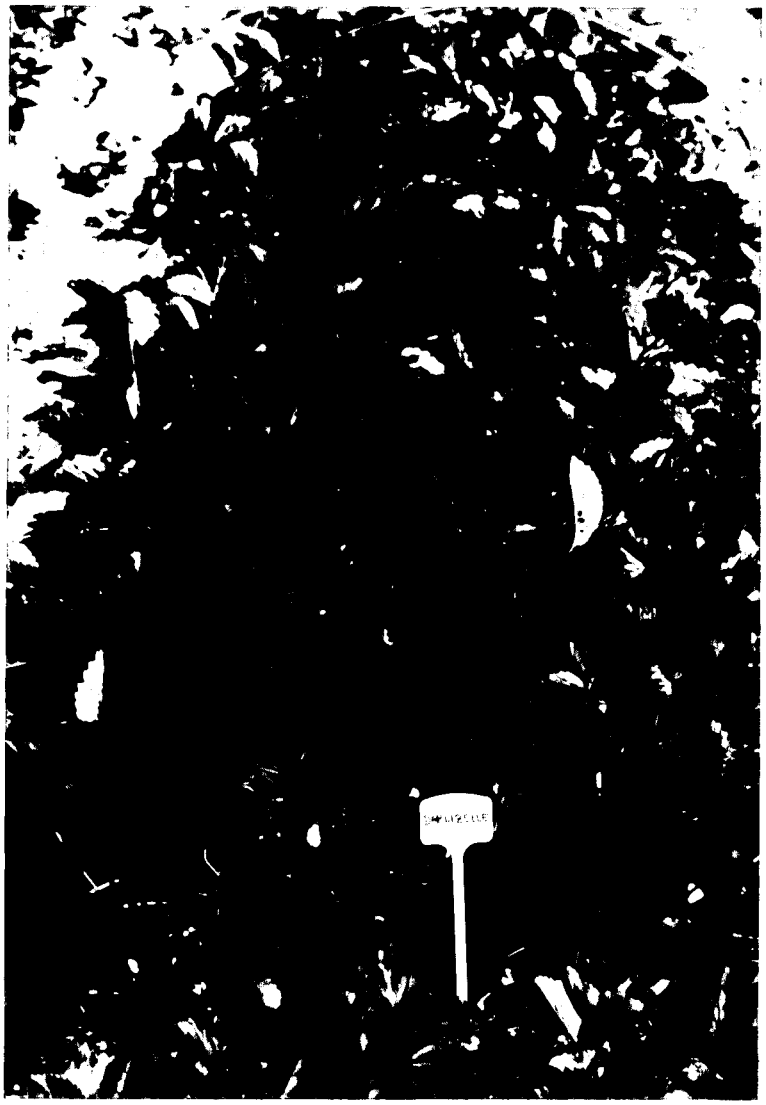

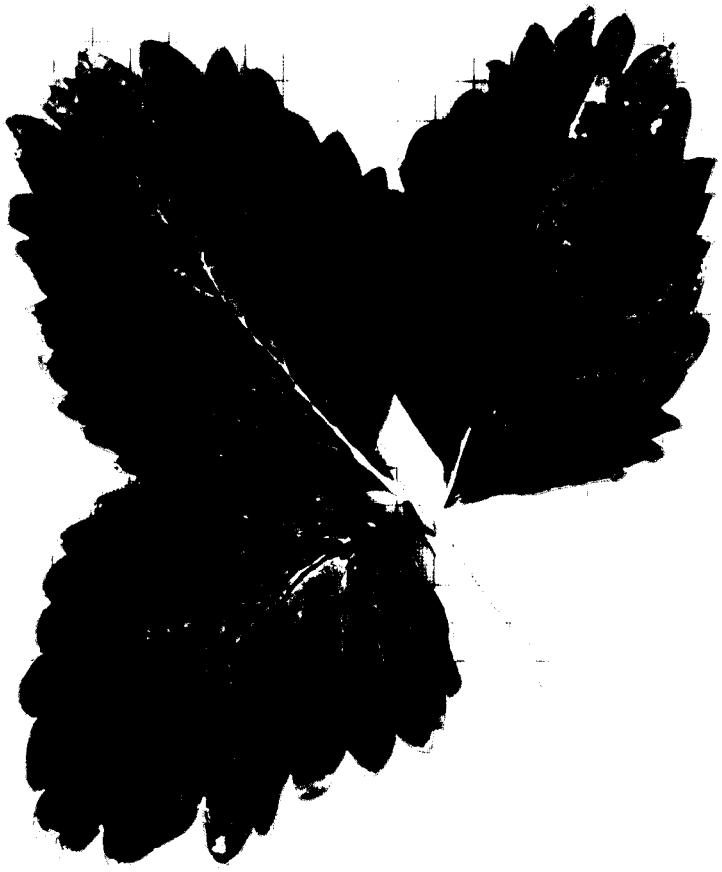

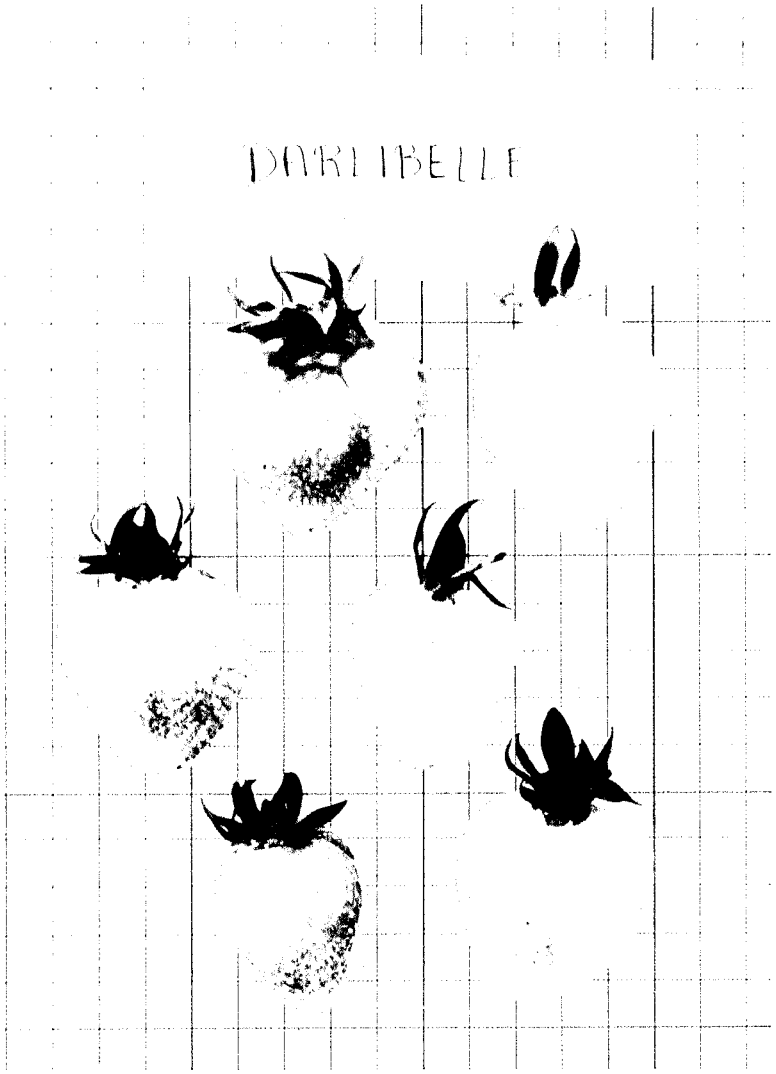
DARLIBELLE